United States Patent [19]
Wamsiedler et al.

[11] Patent Number: 5,808,181
[45] Date of Patent: Sep. 15, 1998

[54] METHOD FOR TESTING A FILTER IN A DIALYSIS SYSTEM

[75] Inventors: Ralf Wamsiedler, Schonungen; Bernd Mathieu, Spiesen-Elversberg, both of Germany

[73] Assignee: Fresenius AG, Germany

[21] Appl. No.: 697,842

[22] Filed: Aug. 29, 1996

[30] Foreign Application Priority Data

Sep. 16, 1995 [DE] Germany .................. 195 34 417.0

[51] Int. Cl.⁶ .................. G01N 15/08; B01D 11/00; A61M 37/00
[52] U.S. Cl. .................. 73/38; 210/646; 604/4
[58] Field of Search .................. 73/38; 210/646; 604/5, 4

[56] References Cited

U.S. PATENT DOCUMENTS

| | | | |
|---|---|---|---|
| 4,614,109 | 9/1986 | Hofmann . | |
| 4,702,829 | 10/1987 | Polaschegg et al. | 210/195.2 |
| 4,872,974 | 10/1989 | Hirayama et al. . | |
| 5,353,630 | 10/1994 | Soda et al. | 73/38 |
| 5,580,460 | 12/1996 | Polaschegg | 210/646 |
| 5,591,344 | 1/1997 | Kenley et al. | 210/636 |
| 5,594,161 | 1/1997 | Randhahn et al. | 73/38 |
| 5,660,722 | 8/1997 | Nederlof | 210/90 |
| 5,674,404 | 10/1997 | Kenley et al. | 210/741 |

FOREIGN PATENT DOCUMENTS

| | | |
|---|---|---|
| 0 491 981 A1 | 7/1992 | European Pat. Off. . |
| 0 83 05 713.7 | 1/1986 | Germany . |
| 3448262 C2 | 6/1986 | Germany . |
| 42 39 937 | 6/1994 | Germany . |

*Primary Examiner*—Hezron E. Williams
*Assistant Examiner*—Jay L. Politzer
*Attorney, Agent, or Firm*—Townsend and Townsend and Crew LLP; Kenneth R. Allen

[57] ABSTRACT

A method for testing filters arranged in the dialysis solution system of an extracorporeal blood treatment apparatus is described, in which the filter membrane being tested is fully wetted with an aqueous solution, in which the branch of the dialysis solution system housing one of the two chambers of the filter being tested is closed off from the remaining branches, in which gas is conducted into the closed-off branch until a predetermined excess pressure has formed in the one chamber of the filter being tested. Simultaneously, the aqueous solution previously conducted into the chamber to fully wet the filter membrane is expelled. The excess pressure in the one chamber of the filter is monitored, in which the pressure drop per unit time is compared with a given reference value which is characteristic of a fully intact filter membrane. If the reference value is exceeded, this provides and indication of a leak in the filter membrane. Further, a dialysis solution system of an extracorporeal blood treatment apparatus is described which comprises at least one filter (16, 35) and a means (21) for closing off a branch of the dialysis solution system housing one of the two chambers (18, 37) of the filter (16, 35) from the remaining branches of the dialysis solution system. The dialysis solution system also includes an air pump (42) for conducting air through at least one hydrophobic filter (43) in the closed-off branch of the dialysis solution system. Moreover, a monitoring device (56) is provided which compares the pressure drop value measured by a pressure sensor (54) and signals a leak in the filter membrane being tested if the given reference value is exceeded.

14 Claims, 2 Drawing Sheets

METHOD FOR TESTING A FILTER IN A DIALYSIS SYSTEM

BACKGROUND OF THE INVENTION

The invention relates to a method for testing at least one filter arranged in a dialysis solution system of an extracorporeal blood treatment apparatus, the filter being divided by a germ-retaining membrane into a first chamber and a second chamber. Further, the invention relates to a dialysis solution system of an extracorporeal blood treatment apparatus containing at least one filter which is divided by a germ-retaining membrane into a first chamber and a second chamber.

In hemodiafiltration, in a manner similar to hemodialysis, blood is conducted past the membrane of a hemofilter, part of the serum being withdrawn via the membrane. This part is replaced by a sterile substitution liquid which is added to the extracorporeal blood path either upstream of the dialyzer (predilution) or downstream of the dialyzer (postdilution). In addition, in the diafiltration the usual hemodialysis is carried out, i.e. dialysis solution is conducted past the membrane of the hemodialyzer so that across the membrane an exchange of substances usually eliminated with urine can take place.

The dialysis solution may be prepared on-line from fresh water and an electrolyte concentrate and the substitution solution on-line from the dialysis solution. The electrolyte concentrate is sterile and the fresh water usually contains no germs, but it is not ensured that the dialysis solution prepared on-line is absolutely sterile and pyrogenfree. For this reason the dialysis solution used in preparing the substitution solution is transformed into a sterile and pyrogen-free state. In addition, upstream of the dialyzer dialysis solution is withdrawn and passed through at least one filter which is divided by a germ-retaining hydrophilic membrane into two chambers. An apparatus of this type which includes filters arranged in the dialysis solution system is known, for example, from DE 34 44 671 C2.

In order to test the seal of the filters of a hemodialysis apparatus known from DE 34 44 671 C2 an ultrafiltration pump arranged in the dialysis solution circuit is actuated to deliver air through a hydrophobic, microporous filter into one of the two chambers, respectively, of the filters. Since the membranes of both filters are already wetted by an aqueous solution during integrity testing which precedes the flush cycle, it is impossible for the inflowing air to escape past the membranes of the filters. Thus the partial vacuum produced by the ultrafiltration pump can be used to test the membranes for any potential leaks. The ultrafiltration pump is actuated until a specific partial vacuum has formed in the solution-filled portion of the dialysis solution system. Thereafter, the change in partial vacuum is monitored by a pressure gauge and the time required for the pressure to increase to a specific value relative to atmospheric pressure is measured. A leak is indicated if the preset time span is exceeded. It is also feasible, however, to evaluate the level of partial vacuum attained after a predetermined time span (forward flow test). A method of this kind for testing a filter seal in a hemo(dia)filtration apparatus known in DE 34 44 671 C2 is described in German patent publication DE 34 48 262 C2. In practice, the partial vacuum test has proved fundamentally reliable, nevertheless the length of the testing phase has proven to be a drawback. Approximately 3 minutes are required for fluid withdrawal in known methods. The total testing time amounts to approximately 10 minutes.

SUMMARY OF THE INVENTION

An object of the present invention is to provide a method for rapidly and safely testing at least one filter for leaks, the filter being arranged in a dialysis solution system of an extracorporeal blood treatment apparatus. A further object of the present invention is to design a dialysis solution system of an extracorporeal blood treatment apparatus that will enable rapid and safe testing of filter seals.

The objectives are achieved according to the present invention by the features set forth in claims 1 to 5 below.

The method according to the present invention is based on a test for measuring excess pressure. In the method according to the present invention the filter membrane is fully wetted with an aqueous solution and gas is conducted into the branch of the dialysis solution system housing one of two chambers of the filter until a predetermined excess pressure builds up in said chamber. This forces the aqueous solution, which is conveyed into the chamber prior thereto and used to fully moisten the filter membrane, past the filter membrane and out of the chamber. The excess pressure in the chamber is then monitored in order to provide information on the integrity of the membrane. When the pressure drops within a predetermined time period to a value lower than a minimum predetermined value, this provides an indication of a leak in the membrane. It is also feasible, however, to measure the time span required for the pressure to drop to a predetermined value.

Dialysis solution as it is found in the dialysis solution system during operation of the blood treatment apparatus may be used as an aqueous solution for wetting the membrane. It is possible to test the filter, e.g. advantageously following the rinse phase of the blood treatment apparatus when the filter membrane is fully wetted with the rinse solution.

A number of unexpected advantages result when testing by means of excess pressure a filter arranged in the dialysis solution system of an extracorporeal blood treatment apparatus.

First, substantially greater pressure differentials may be produced using excess pressure, thereby enhancing significantly the sensitivity of the test. In practice, the pressure difference may total 4 bars while theoretically the maximum partial vacuum possible in the dialysis solution system may only be 1 bar. In known testing methods the partial vacuum generated in parts of the dialysis solution system equals as little as 0.3 bars. It is also possible using the method according to the present invention to detect small tears in the membrane. Compared to a test using a partial vacuum, the sensitivity is increased three- to fourfold.

Further, the resiliency of a tube is much less at excess pressures than in a partial vacuum, resulting in a more rigid system. Since gas delivery pumps have a higher pumping output, it is possible to rapidly fill that part of the dialysis solution system which is being ventilated with gas. An initial excess pressure builds immediately during initial measurements. Said pressure equals in practice 0.8 bars and increases rapidly to the measuring pressure.

It is advantageous to build up excess pressure using an air pump with a delivery rate that is higher than the delivery rate of an ultrafiltration pump arranged in the dialysis solution system, the latter of which is used to generate a partial vacuum in the method known from German patent publication DE 34 48 262 C2. The test pressure may form within approximately 10 to 15 seconds, so that by using the method according to the present invention the overall testing time may be limited to approximately 60 seconds.

Particularly advantageous is the fact that in the method according to the present invention post degasification does not lead to a falsification of test results. Although dialyzate itself is degassed, the solution is degassed again as a filter is being tested if the partial vacuum is formed too rapidly or is too high. To eliminate problems of this type arising during evaluation, it is essential to restrict substantially the pressure difference during measurement of the partial vacuum. Moreover, it takes a significant amount of time during a partial vacuum test before the actual measuring pressure is reached. Furthers it is impossible to conduct a pressure retaining test when the dialysis solution system is being disinfected or rinsed, since this would also result in post degasification of the fluids. Conversely, it is possible to conduct a test of the filter in accordance with the present invention by means of excess pressure at any time and using any desirable fluid.

It is possible to convey the aqueous solution used to wet the membrane of the filter being tested by means of a delivery pump conventionally arranged in the dialysis solution system of an extracorporeal blood treatment apparatus. To shut off the branch of the dialysis solution system containing one of the two chambers of the filter with a pressure-tight seal, electromagnetically activated shut-off valves are preferably used. The excess pressure is monitored by a monitoring apparatus which compares the value of the pressure drop per unit time with a predetermined reference value and signals a leak if the predetermined value is exceeded.

A preferred embodiment of the present invention is described in greater detail below with reference to the drawings.

DETAILED DESCRIPTION OF A PREFERRED EMBODIMENT

Figure 1:
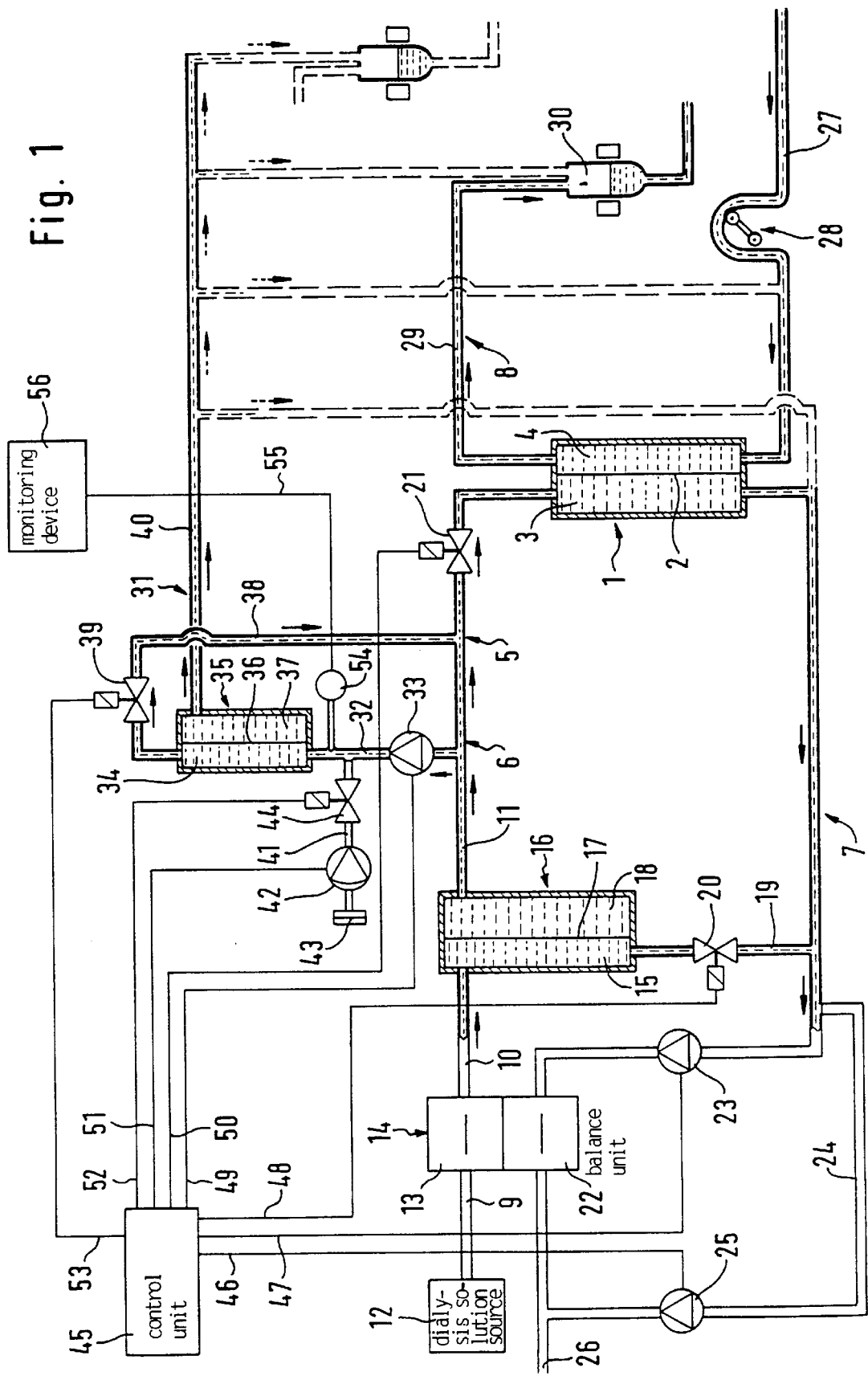
FIG. 1 illustrates schematically a hemo(dia)filtration apparatus with a dialysis solution system containing two filters.

FIG. 1 illustrates schematically the essential components of a hemo(dia)filtration apparatus which allows multiple blood treatment methods to be carried out. The dialysis solution system of the extracorporeal blood treatment apparatus consists of a dialyzer 1 which is divided by a membrane 2 into a first chamber 3 traversed by the dialysis solution and a second chamber 4 traversed by the blood.

The first chamber 3 is connected into a dialysis solution path 5 of the dialysis solution system which consists of a supply line 6 and a discharge line 7, while the second chamber 4 is connected into a blood path 8.

The supply line 6 of dialysis solution path 5 consists of a first supply line segment 9, a second supply line segment 10 and a third supply line segment 11, and it connects a dialysis solution source 12 with the first chamber 3 of dialyzer 1.

The first supply line segment 9 connects the dialysis solution source 12 to the first balance chamber 13 of a balance unit 14. The first balance chamber 13 of balance unit 14 is connected by the second supply line segment 10 to the inlet of the first chamber 15 of a first filter 16 which is divided by a germ-retaining, hydrophilic membrane 17 into a first and second chambers 15, 18. The outlet of the first chamber 15 is linked to discharge line 7 by a bypass line 19 into which an electromagnetically activated bypass valve 20 is connected.

The second chamber 18 of the first filter 16 is connected via the third supply line segment 11 to the inlet of the first chamber 3 of dialyzer 1. Connected into the third supply line segment 11 is an electromagnetically activated dialyzer valve 21. Discharge line 7 leads from the outlet of the first chamber 3 of dialyzer 1 to the second balance chamber 22 of balance unit 14, and disposed in said discharge line is a dialysis solution pump 23. Branching from discharge line 7 upstream of the dialysis solution pump 23 is an ultrafiltration line 24 in which an ultrafiltration pump 25 is arranged for withdrawing dialysis solution. Ultrafiltration line 24 leads to a drain 26 to which the outlet of the second balance chamber 22 of balance unit 14 is also connected.

Blood path 8 includes a blood supply line 27 leading away from the patient which is connected to the inlet of the second chamber 4 of dialyzer 1. Connected into blood supply line 27 is a pump 28. The outlet of the second chamber 4 of dialyzer 1 leads via the first section of a blood discharge line 29 to a drip chamber 30 from where blood is conveyed to the patient via the second section of blood discharge line 29.

Further, the dialysis solution system includes a substituate circuit 31 which branches off from the third supply line segment 11 of dialysis solution path 5 upstream of dialyzer-valve 21, and leads by way of a first line segment 23 into which a substituate pump 32 is connected to the outlet of the first chamber 34 of a second filter 35 which is divided by a germ-retaining, hydrophilic membrane 36 into a first and a second chamber 34, 37. Branching off from the outlet of the first chamber 34 of the second filter 35 is a connecting line 38 which is connected to supply line 6 of the dialysis solution path 5 upstream of dialyzer valve 21. Disposed in said connecting line 38 is an electromagnetically activated shut-off valve 39.

The second segment 40 of the substituate circuit 31 branches off from the second chamber 37 of the second filter 35 and may be selectively connected to either blood supply line 27 (predilution), to drip chamber 30 (postdilution) or to discharge line 7 for purposes of flushing the dialysis solution system and for testing membranes 17, 36 of the filter arranged in the dialysis solution system. The individual connecting branches are illustrated in FIG. 1 by dashed lines. Finally, the blood treatment apparatus may also function as a hemofiltration apparatus. In such case the dialyzer-valve 21 is closed.

From the first line segment 32 of substituate circuit 31 yet another line 41 branches off which is connected to the air outlet of an air pump 42. The air inlet of air pump 42 is linked by way of a hydrophobic sterile filter 43 to the ambient air. Disposed in line 41 is an electromagnetically activated shut-off valve 44.

Also provided is a control unit 45 which is connected by control lines 46 to 53 to ultrafiltration pump 25, dialysis solution pump 23, substituate pump 33, air pump 42, bypass valve 20, dialyzer valve 21, retaining valve 39 and shut-off valve 44 disposed in line segment 41 of air pump 42. Connected to the first line segment 32 of substituate circuit 31 is a pressure sensor 54 which is linked by a signal line 55 to a monitoring device 56.

The operation of the hemodiafiltration apparatus is described as follows.

Fresh dialysis solution is pumped from the dialysis solution source 12 through the first balance chamber 13 of balance unit 14 and the first filter 16 into the first chamber 3 of the dialyzer. Germs and pyrogens transported by the fresh dialysis solution into supply line 6 are filtered out by membrane 17 of the first filter 16 and are deposited on the former. By opening the bypass valve 20 in bypass line 19 to establish a link from the first chamber 15 of filter 16 to discharge line 7, the first chamber 15 is flushed with dialysis solution such that germs and pyrogens deposited on the membrane are transported by the dialysis solution and flushed into the drain.

Figure 2:
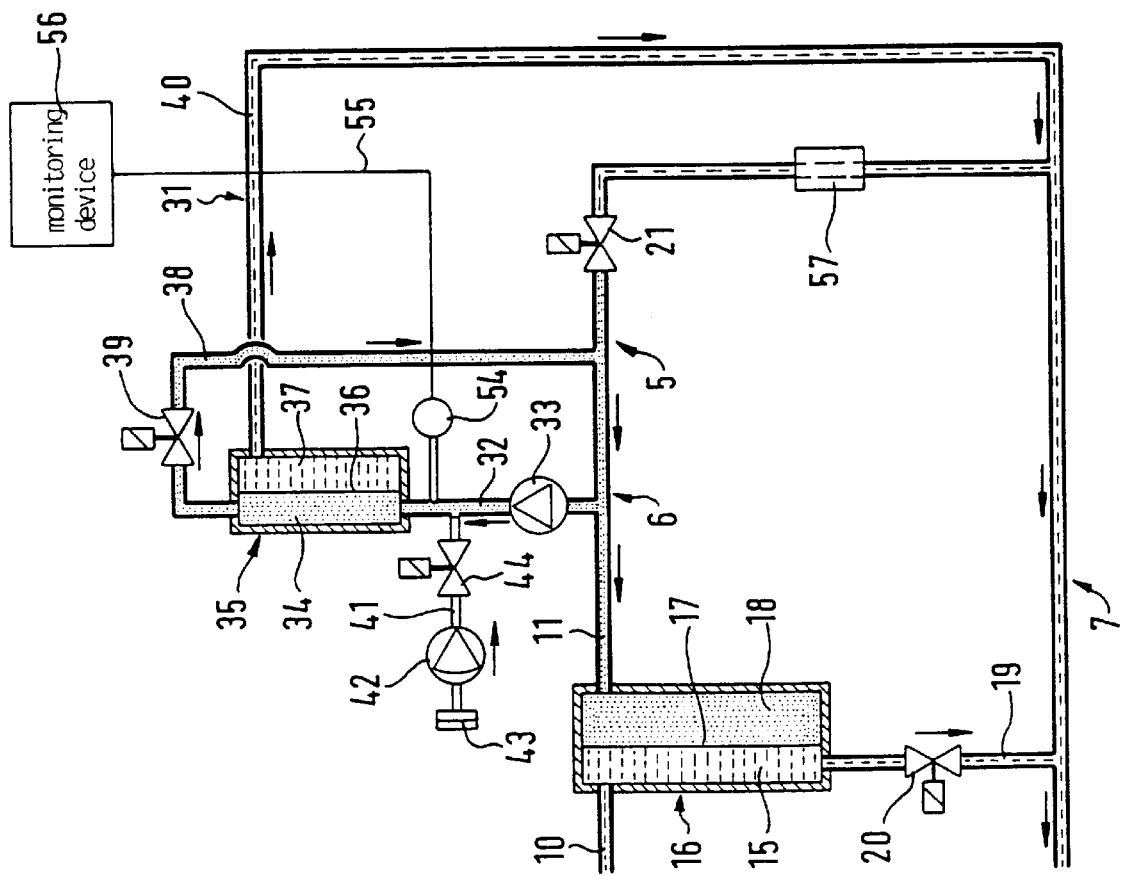
FIG. 2 shows the dialysis solution system of the hemo (dia)filtration apparatus during the test phase.

After substitute pump 33 is switched on, dialysis solution is withdrawn through membrane 36 of the second filter 35 in supply line 6 of the dialysis solution path and conveyed to blood path 8. Membrane 36 of the second filter 35 is flushed by opening a check valve 39 disposed in connecting line 38 between first chamber 34 of the second filter 35 and supply line 6 of the dialysis solution path. During the flushing cycle dialyzer-valve 21 is opened and a short-circuit piece 57 is connected to the conduit system in place of dialyzer 1 (FIG. 2).

The method for testing the seal of filters 16, 35 arranged in dialysis solution system 5 is described as follows.

First, the lines of the dialysis solution system are filled with dialysis solution by actuating dialysis solution pump 23, to thereby completely moisten membranes 17, 36 of the first and second filters 16, 35 with an aqueous solution, rendering them impermeable to gas. Testing of the integrity of membranes 17, 36 may, for example, be carried out immediately after the dialysis solution system is flushed. FIG. 2 illustrates a dialysis solution system of the hemo(dia)filtration apparatus in which substitute circuit 31 is connected to discharge line 7 and, in place of the first chamber 3 of dialyzer 1, a short-circuit piece 57 is connected into the dialysis solution path for carrying out the flushing cycle.

To simultaneously test membranes 17, 36 of both filters 16, 35 for leaks, dialyzer-valve 21 is closed and bypass valve 20 is opened. In addition, retaining valve 39 disposed in connecting line 32 between first chamber 34 of the second filter 35 and the supply line 6 is opened, and check valve 44 disposed in front of air pump 42 is also opened. Further, substitute circuit 31 is connected to discharge line 7 which leads to drain 26. At this point air pump 42 is actuated, air is drawn through the hydrophobic sterile filter 43 and conducted into the branch of the dialysis solution system which houses the second chamber 18 of the first filter 16 and the first chamber 34 of the second filter 35. An excess pressure then builds in both chambers 18, 34 of filters 16, 35 and in the adjacent line segments, i.e. in connecting line 32 and the third line segment 11 of supply line 6.

In the process, dialysis solution disposed in the first chamber 34 of the second filter 35 and in the second chamber 18 of the first filter 16 as well as in adjacent line segments is then expelled through the membranes 17, 36 of both filters 16, 35. The dialysis solution flows via connecting line 38 and the first chamber 15 of the first filter 16 through bypass line 19 into discharge line 7 which leads to drain 26, and via the second chamber 37 of the second filter 35 and the section 40 of substitute circuit 31 into discharge line 7 which leads to drain 26. Once a predetermined excess pressure has formed in the separated branch of the dialysis solution system, air pump 42 is switched off.

In the monitoring device 56 the excess pressure detected by the pressure sensor 54 is monitored and the pressure drop is recorded within a predetermined time period. Then the pressure drop per unit time is compared with a predetermined reference value which is characteristic of a pressure drop per unit time of an intact filter membrane. If the pressure drop within the predetermined time period is greater than the reference value, the monitoring device emits an acoustical and/or optical alarm signal. In such case the one and/or other filter membrane is leaking. Alternatively, it is also feasible to test just the membrane of one or multiple filters using the method according to the present invention. For this purpose shut-off members are provided in the line segments which permit a build up of excess pressure only in the chamber of the filter being tested. Theoretically, it is also possible to test the dialyzer itself in the same manner, but this should never be done when patients are connected to the blood line.

The electromagnetically activated valves 20, 21, 39, and 44 are controlled fully automatically and air pump 42 is automatically set into operation in accordance with a preset program by control unit 45 of the hemo(dia)filtration apparatus illustrated in FIG. 1.

What is claimed is:

1. A method for testing at least one filter arranged in a dialysis solution system of an extracorporeal blood treatment apparatus, the filter being divided by a germ-retaining membrane into a first chamber and a second chamber, the method comprising steps of:

filling at least one branch of the dialysis solution system with an aqueous solution, the aqueous solution fully wetting the germ-retaining membrane of the filter, sealing off the one branch of the dialysis solution system from remaining branches of the dialysis solution system, wherein the one branch houses the first chamber of the filter, conducting gas into the one branch of the dialysis solution system housing the first chamber to expel fluid through the germ-retaining membrane of the filter, shutting off the supply of gas once a predetermined pressure is formed in the first chamber, and monitoring a rate of change of pressure in the first chamber of the filter to provide information on membrane integrity.

2. A method according to claim 1, characterized in that the aqueous solution used to wet the membrane of the filter comprises dialysis solution.

3. A method according to claim 1, characterized in that the gas comprises ambient airs, the gas being conducted through at least one hydrophobic filter in the one branch of the dialysis solution system housing the first chamber.

4. A method according to claim 1, further comprising a step of comparing a pressure rate of change to a reference value, and indicating a leak condition if said pressure rate of change exceeds said reference value.

5. A dialysis solution system of an extracorporeal blood treatment apparatus containing at least one filter (16, 35) that is divided by a germ-retaining membrane (17, 36) into a first chamber (15, 34) and a second chamber (18, 37), the dialysis solution system comprising:

means (23) for conveying an aqueous solution into at least one branch of the dialysis solution system while membrane (17, 36) of the filter or filters (16, 35) being tested is fully wetted, means (21) for closing off a branch of the dialysis solution system housing one of the two chambers (18, 37) of the filter or filters (16, 35) from remaining branches of the dialysis solution system, means (42) for conducting a gas into the branch of the dialysis solution system housing the one chamber (18, 34) of the filter or filters (16, 35), while fluid is expelled through the membrane (17, 36) of the filter or filters (16, 35), and a monitoring device (56) for monitoring a rate of change of pressure in the one chamber (18, 34) of the filter or filters (16, 35).

6. A dialysis solution system according to claim 5, characterized in that the means for conducting gas is an air pump (42) that draws ambient air through at least one hydrophobic filter (43).

7. A dialysis solution system according to claim 5, characterized in that the monitoring device (56) compares a pressure rate of change with a reference value, and signals a leak if the pressure rate of change exceeds the reference value.

8. A method according to claim 2, characterized in that gas in the form of ambient air is conducted through at least one hydrophobic filter in the branch of the dialysis solution system housing the one chamber of the filter or filters.

9. A method according to claim 2, characterized in that a pressure rate of change is compared to a reference value, indicating a leak if said pressure rate of change exceeds said reference value.

10. A method according to claim 3, characterized in that a pressure rate of change is compared to a reference value, indicating a leak if said pressure rate of change exceeds said reference value.

11. A method according to claim 8, characterized in that a pressure rate of change is compared to a reference value, indicating a leak if said pressure rate of change exceeds said reference value.

12. A dialysis solution system according to claim 6, characterized in that the monitoring device (56) compares a pressure rate of change with a reference value, and signals a leak if the pressure rate of change exceeds the reference value.

13. A method for testing a filter in a dialysis section of an extracorporeal blood treatment apparatus, the filter being divided by a germ-retaining membrane into a first chamber and a second chamber, the method comprising steps of:

filling the first chamber with dialysis solution through a branch of the dialysis solution system to fully wet the germ-retaining membrane;

sealing off the branch and the first chamber from remaining branches of the dialysis solution system;

pumping hydrophobically filtered ambient air into the branch to expel dialysis solution through the germ-retaining membrane;

shutting off the pumping of the hydrophobicaly filtered ambient air once a predetermined pressure is formed in the first chamber;

monitoring a chamber pressure in the first chamber to determine a pressure rate of change;

comparing the pressure rate of change against a reference value; and indicating a filter problem if the pressure rate of change exceeds the reference value.

14. A dialysis solution system of an extracorporeal blood treatment apparatus, the dialysis solution system comprising:

a filter divided into a first chamber and a second chamber by a germ-retaining membrane;

a first conduit for conveying dialysis solution into the first chamber to fully wet the germ-retaining membrane;

a valve configured to selectively seal a branch of the dialysis solution system including the first chamber from a remaining branch of the dialysis solution system;

a pump configured to conduct ambient air through a hydrophobic filter to the branch of the dialysis solution system to expel dialysis solution through the germ-retaining membrane; and a pressure monitoring device coupled to the branch of the dialysis solution system, the pressure monitoring device capable of monitoring the pressure in the first chamber of the filter.

* * * * *